(12) United States Patent
Allen et al.

(10) Patent No.: US 8,672,835 B2
(45) Date of Patent: Mar. 18, 2014

(54) PROPELLABLE APPARATUS AND RELATED METHODS

(75) Inventors: John J. Allen, Mendota Heights, MN (US); Tracee Elizabeth Eidenschink, Wayzata, MN (US); Charles A. Brantingham, St Paul, MN (US); Richard Cornelius, Wayzata, MN (US)

(73) Assignee: FUJIFILM Corporation, Tokyo (JP)

( * ) Notice: Subject to any disclaimer, the term of this patent is extended or adjusted under 35 U.S.C. 154(b) by 368 days.

(21) Appl. No.: 13/102,388

(22) Filed: May 6, 2011

(65) Prior Publication Data

US 2011/0265681 A1      Nov. 3, 2011

Related U.S. Application Data

(63) Continuation-in-part of application No. 12/706,339, filed on Feb. 16, 2010.

(60) Provisional application No. 61/152,780, filed on Feb. 16, 2009.

(51) Int. Cl.
*A61B 1/00*         (2006.01)

(52) U.S. Cl.
USPC .......................................... 600/114; 600/115

(58) Field of Classification Search
USPC .......................................... 600/114, 115, 116
See application file for complete search history.

(56) References Cited

U.S. PATENT DOCUMENTS

| | | | |
|---|---|---|---|
| 6,971,990 | B2 | 12/2005 | Ziegler et al. |
| 2006/0089533 | A1 | 4/2006 | Ziegler et al. |
| 2008/0045790 | A1 | 2/2008 | Ziegler et al. |
| 2009/0227838 | A1 | 9/2009 | Allen et al. |
| 2009/0233747 | A1 | 9/2009 | Sheridan et al. |

*Primary Examiner* — Rochelle-Ann J Blackman
(74) *Attorney, Agent, or Firm* — Sughrue Mion, PLLC

(57) ABSTRACT

Propellable apparatus, assemblies and related methods including a self-enclosed member are disclosed. The self-enclosed member can include an inner surface at least partially defining an enclosed region, and an outer surface that turns outwardly to engage a cavity or lumen wall in addition to turning inward to at least partially encompass a central region defining a longitudinal path. The apparatus can include an internal drive mechanism engageable with the outer surface of the self-enclosed member to provide relative movement between the self-enclosed member and the cavity or lumen wall. A tapered member, positioned on the apparatus adjacent an end of the self-enclosed member, can provide a size transition between an outer surface portion of the self-enclosed member and an outer surface of a payload insertable within the central region. In some examples, one or more reinforcing members can be integrated within the self-enclosed member for increased durability and rotational use.

15 Claims, 14 Drawing Sheets

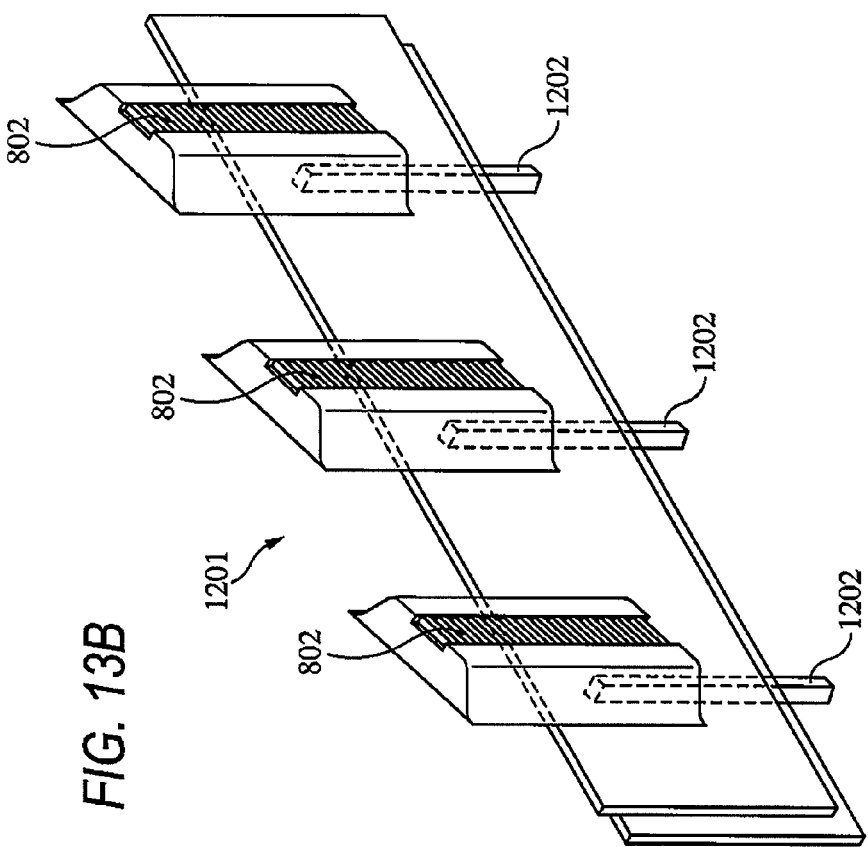
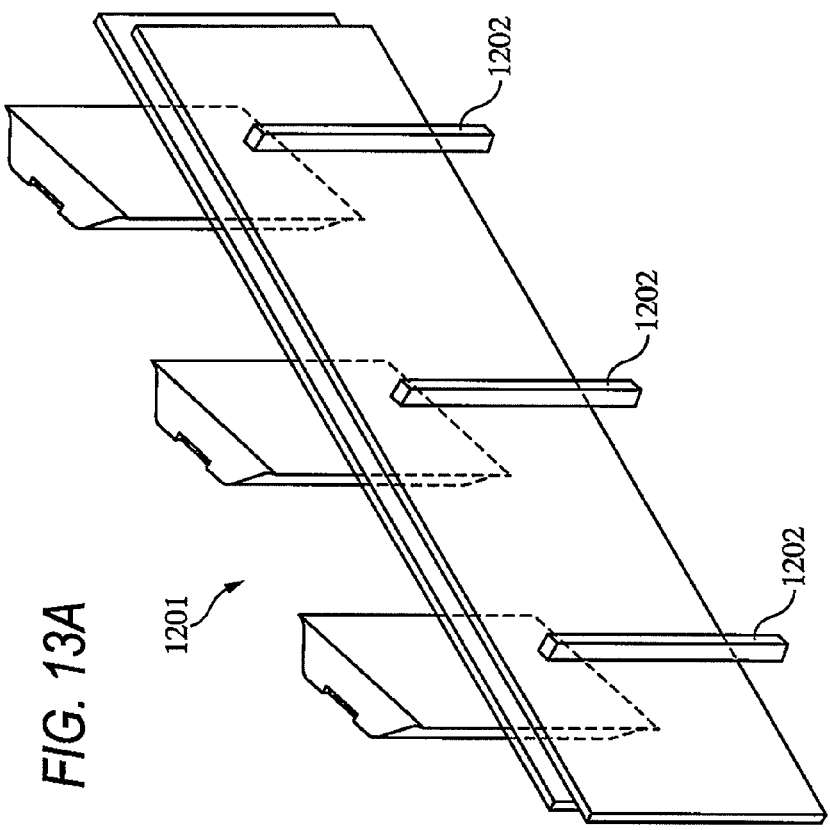

PROPELLABLE APPARATUS AND RELATED METHODS

RELATED APPLICATIONS

The present application is a continuation-in-part of U.S. patent application Ser. No. 12/706,339, filed on Feb. 16, 2010 which, in turn, claims the benefit of Provisional Patent Application Ser. No. 61/152,780, filed on Feb. 16, 2009. The entire disclosure of the above-mentioned application is hereby incorporated by reference.

TECHNICAL FIELD

This patent document pertains generally to an apparatus configured to facilitate carrying a payload. More particularly, but not by way of limitation, this patent document pertains to a propellable apparatus configured to facilitate carrying a payload, such as an endoscope or other instrument, into a body or non-body cavity or lumen.

BACKGROUND

An endo scope is an instrument often used in medical procedures to view a location of interest within a subject's body and transmit such view(s) to a caregiver or other observer. Endo scopes can also be used to perform a variety of diagnostic and interventional procedures, such as biopsies and other small surgical procedures. Examples of endo scopes include a colono scope configured for use within the colon, an entero scope configured for use within the stomach or small bowel, and a bronchoscope configured for use within the trachea or bronchi. Endo scopes are typically inserted into body cavities or lumens via a natural bodily orifice, but can also be inserted via a surface incision to gain access to the internal location of interest.

Overview

One approach in facilitating advancement of an endo scope or other similar payload instrument into, within, and out of a cavity or lumen includes using a propellable apparatus, such as described in Ziegler et al. U.S. Pat. No. 6,971,990, entitled "PROPULSION MECHANISM FOR ENDOSCOPIC SYSTEMS;" Ziegler et al. U.S. Patent Application Publication No. 2006/0089533, entitled "SELF-PROPELLABLE APPARATUS AND METHOD;" Ziegler et al. U.S. Patent Application Publication No. 2008/0045790, Attorney Docket No. 2568.002US2, entitled "SELF-PROPELLABLE ENDOSCOPIC APPARATUS AND METHOD;" Sheridan U.S. Patent Application Publication No. 2009/0233747, entitled "TORQUE-ADJUSTING DRIVE MECHANISM FOR A DEVICE;" Allen et al. U.S. Patent Application Publication No. 2009/0227838, entitled "PROPELLABLE APPARATUS WITH PASSIVE SIZE CHANGING ABILITY;" and Eidenschink et al. U.S. Patent Application No. 61/243,208, entitled "PROPELLABLE APPARATUS WITH ACTIVE SIZE CHANGING ABILITY," the disclosures of each of which are herein incorporated by reference in their entirety, including their descriptions of a propellable apparatus and related methods.

In various examples, a drive structure including one or more drive members and gear or wheel power couplings can be mounted on the endoscope or other payload instrument. The drive structure can propel a self-enclosed member (e.g., self-enclosed tube, such as a toroidial membrane, or self-enclosed strips) to create propulsion force against a cavity or lumen wall. This propulsion force can aid in advancing or withdrawing the endoscope or other payload instrument relative to a cavity or lumen wall.

In some examples, the propellable apparatus comprises a permeable self-enclosed member; while in other examples, the propellable apparatus comprises an impermeable self-enclosed member. The self-enclosed member can be sized and shaped to fit within and engage a cavity or lumen wall. The self-enclosed member can comprise an inner surface defining an enclosed region, and an outer surface that turns outward to engage the cavity or lumen wall in addition to turning inward to encompass a central region defining a concentric longitudinal path. An attachment can be coupled to the self-enclosed member. The attachment can be configured to secure engagement between an endoscope or other payload instrument and the self-enclosed member. The self-enclosed member can be powered to provide movement relative to the cavity or lumen wall. This can help move the payload, with respect to the cavity or lumen, in at least one of a forward or reverse direction with respect to the defined longitudinal path.

Various options for the above-referenced propellable apparatus are available, each of which can be beneficial in certain applications and circumstances. In some examples, the attachment between the propellable apparatus and the payload is made at a front-end tip portion of the payload. This can be advantageous for advancing the payload through sharp bends in a body cavity or lumen. In some examples, the propellable apparatus can be made to have a relatively short length (e.g., between about 0.8 inches and about 1.5 inches) so-as-to not limit the articulation of a payload, having a separately controllable articulating capability, when it is mounted at or near the front-end thereof. In some examples, the one or more drive members can be made of flexible cables including wrapped filaments instead of solid wire to allow greater flexing of the drive members without reaching unacceptable internal stress levels. In some examples, an additional component such as a wiper can be added to at least one end of the propellable apparatus, thereby shielding tissue from the apparatus drive mechanism. In some examples, a tapered member (e.g., a wedge-shaped member) can be added behind the propellable apparatus to provide a size transition from the outer surface of the payload to the larger diameter, outer surface of the self-enclosed member (e.g., tube), thereby easing withdrawn of the apparatus from the cavity or lumen. The tapered member can be passively or actively (e.g., actuatably) expanded and contracted, as needed or as desired. In some examples, different reinforcing members may be used for the rotating, self-enclosed member to improve its durability and rotational use.

To better illustrate the present propellable apparatus, a non-limiting list of examples is provided here:

In Example 1, a propellable apparatus comprises a self-enclosed member configured to fit within and partially engage a cavity or lumen wall, the self-enclosed member including an inner surface at least partially defining an enclosed region, and an outer surface that turns outwardly to engage the cavity or lumen wall in addition to turning inward to at least partially encompass a central region defining a longitudinal path; an internal drive mechanism engageable with the outer surface of the self-enclosed member, thereby providing relative movement between the self-enclosed member and the cavity or lumen wall; and a tapered member positioned adjacent an end of the self-enclosed member, the tapered member providing a size transition from the end of the self-enclosed member to a diametrically smaller, outer surface of a payload insertable within the central region.

In Example 2, the propellable apparatus of Example 1 is optionally configured such that the tapered member is actively expandable or contractible.

In Example 3, the propellable apparatus of Example 2 is optionally configured such that the tapered member comprises a conically-shaped, actively inflatable balloon.

In Example 4, the propellable apparatus of Example 3 optionally comprises one or more tubular members configured to move a fluid into or out of the inflatable balloon for size adjustment use.

In Example 5, the propellable apparatus of any one or any combination of Examples 1-4 is optionally configured such that the inflatable balloon includes at least one groove configured to house one or more elongate or tubular members (e.g., elongate drive members engagable with the internal drive mechanism or tubular members configured to move the fluid into or out of the inflatable balloon).

In Example 6, the propellable apparatus of any one or any combination of Examples 1-5 is optionally configured such that the tapered member includes a wedge-like cross-sectional shape when viewed in a longitudinal direction.

In Example 7, the propellable apparatus of any one or any combination of Examples 1-6 is optionally configured such that the tapered member is coupled adjacent a back-end of the self-enclosed member.

In Example 8, the propellable apparatus of any one or any combination of Examples 1-7 optionally comprises one or more wiper members including an edge configured to press against the outer surface of the self-enclosed member, thereby removing debris as the self-enclosed member turns inward.

In Example 9, the propellable apparatus of Example 8 is optionally configured such that the edge of the one or more wiper members includes a lubricious coating.

In Example 10, the propellable apparatus of any one or any combination of Examples 1-9 optionally comprises an attachment coupled in proximity to the self-enclosed member, the attachment configured to couple the payload within the central region.

In Example 11, the propellable apparatus of Example 10 is optionally configured such that the payload longitudinally extends from a handle portion to a leading viewing portion, and wherein the self-enclosed member is attached at the leading viewing portion.

In Example 12, the propellable apparatus of any one or any combination of Examples 10 or 11 is optionally configured such that the payload is an endo scope.

In Example 13, the propellable apparatus of any one or any combination of Examples 1-12 optionally comprises one or more drive members configured to transmit externally-generated power to the internal drive mechanism, and wherein the one or more drive members include a plurality of filaments wound in at least a first direction and a second direction, the second direction different than the first direction.

In Example 14, the propellable apparatus of any one or any combination of Examples 1-13 is optionally configured such that the internal drive mechanism is configured to receive power in a first form and convert the first form power to a linear impelling power received by the self-enclosed member.

In Example 15, the propellable apparatus of Example 14 is optionally configured such that the internal drive mechanism includes a worm gear located at least partially within the central region, the worm gear, when powered, configured to impart the linear impelling power to the self-enclosed member via a motive drive wheel or gear.

In Example 16, the propellable apparatus of Example 15 is optionally configured such that the worm gear is coupled to a mechanical power transmission providing a spinning mechanical power, the worm gear configured to partially convert the spinning mechanical power to the linear impelling power.

In Example 17, the propellable apparatus of any one or any combination of Examples 1-16 is optionally configured such that a longitudinal length of the apparatus is less than about 1.5 inches, less than about 1.4 inches, less than about 1.3 inches, less than about 1.2 inches, less than about 1.1 inches, or less than about 1.0 inches, such that the apparatus length is less than a length of a payload's rigid front-end tip portion.

In Example 18, a propellable apparatus comprises a self-enclosed member sized and shaped to fit within and engage a cavity or lumen wall, the self-enclosed member including an inner surface at least partially defining an enclosed region, and an outer surface that turns outwardly to engage the cavity or lumen wall in addition to turning inward to at least partially encompass a central region defining a longitudinal path; and at least one reinforcing member embedded between the inner surface and the outer surface of the self-enclosed member.

In Example 19, the propellable apparatus of Example 18 is optionally configured such that the at least one reinforcing member includes a stiffness or a toughness greater than a stiffness or toughness of the self-enclosed member. The reinforcing member can have a reduced axial elasticity as compared to the surrounding material of the self-enclosed member. Optionally, the reinforcing member can include a mesh configuration to yield relative inelasticity in a direction of rotation with relatively high flexibility in bending.

In Example 20, the propellable apparatus of any one or any combination of Examples 18 or 19 optionally comprises an internal drive mechanism engageable with the outer surface of the self-enclosed member, thereby providing relative movement between the self-enclosed member and the cavity or lumen wall.

In Example 21, the propellable apparatus of Example 20 is optionally configured such that the internal drive mechanism includes one or more gears or wheels, and wherein the at least one reinforcing member is positioned in line with a position of the one or more gears or wheels.

In Example 22, the propellable apparatus of Example 21 is optionally configured such that the outer surface of the self-enclosed member includes one or more tread sections configured to engage with the one or more gears or wheels of the internal drive mechanism.

In Example 23, the propellable apparatus of any one or any combination of Examples 18-22 is optionally configured such that the at least one reinforcing member includes at least one of a peek, a nylon, a polyester or a urethane material.

In Example 24, the propellable apparatus of any one or any combination of Examples 18-23 is optionally configured such that the at least one reinforcing member is molded into the self-enclosed member.

In Example 25, a propellable apparatus comprises means for providing an inner surface and an outer surface which move in opposite directions when the apparatus is in motion, including providing a self-enclosed member defining a central cavity and having an enclosed region, which is configurable to enter into and navigate a cavity or lumen; means for providing a tapered size transition between a member disposable with the central region and an outer surface portion of the self-enclosed member; means for reinforcing a stiffness or toughness of the self-enclosed member; and means for propelling the self-enclosed member using the outer surface.

In Example 26, the propellable apparatus of Example 25 is optionally configured such that the means for reinforcing includes means for decreasing driving force transmission loss to the self-enclosed member, when powered.

In Example 27, the apparatus of any one or any combination of Examples 1-26 is optionally configured such that all elements or options recited are available to use or select from.

These and other examples, advantages, and features of the present propellable apparatus, assemblies and related methods will be set forth in part in following Detailed Description. This Overview is intended to provide an introduction to the subject matter of the present patent document. It is not intended to provide an exclusive or exhaustive explanation of the invention. The Detailed Description is included to provide further information about the present patent document.

BRIEF DESCRIPTION OF THE DRAWINGS

In the drawings, like numerals can be used to describe similar components throughout the several views. Like numerals having different letter suffixes can be used to represent different instances of similar components. The drawings illustrate generally, by way of example, but not by way of limitation, various propellable apparatus embodiments discussed in the present document.

FIGS. 13A and 13B illustrate examples of development views of a tube including a first and second sections, beads, treads, as constructed in accordance with at least one embodiment.

DETAILED DESCRIPTION

The present inventors have recognized, among other things, that a variety of challenges are faced in the area of endoscope advancement through body cavities or lumens. Traditional endoscopes, for example, include a rigid or semi-rigid rod or shaft, which can be inserted into a natural orifice or incision and forced through the associated body cavity or lumen to the location of interest. However, when a body cavity or lumen pathway is constricted, convoluted or consists of many curves, as can be the case with the colon, the stomach or small bowel, it can be difficult or impossible to forcibly push the endoscope to the desired location(s). In addition, the increased force required in traversing through each additional turn or corner of the cavity or lumen pathway raises the risk of subject surgical complications, such as bowel perforation and patient discomfort and pain experienced during or after a procedure.

The present inventors have also recognized that in a field different from medical applications, optical or other payload instruments can be used in non-medical commercial and industrial applications to obtain views, for example, from non-body cavity or lumens, such as sections of pipe or other structures having a number of curves and turns. Such non-body cavity or lumens can be partially occluded or have build-up on an inner surface and thus present an irregular internal shape or diameter impeding advancement of the viewing or other payload instruments.

One promising approach to endoscope or other payload instrument advancement through a body or non-body cavity or lumen can be a propellable apparatus configured to help advance the endoscope or other payload instrument through constricted, convoluted or curved pathways. To this end, the present inventors have recognized that (1) it can sometimes be advantageous to attach the propellable apparatus at a front-end tip portion of a payload, (2) a propellable apparatus having a relatively short length (e.g., between about 0.8 inches and about 1.5 inches) does not limit articulation of a flexible payload, having a separately controllable articulating capability, an appreciable degree when it is mounted at or near the front-end thereof, (3) drive members made of flexible cable including wrapped filaments allows for adequate flexing without reaching unacceptable internal stress levels during rotation, (4) one or more wiper members can be added to the propellable apparatus, such as at one or both apparatus ends to prevent tissue from engaging with the apparatus drive mechanism, (5) a tapered member can be added to a back-end of the propellable apparatus to facilitate removal of the apparatus from a cavity or lumen, and (6) one or more reinforcing members can be integrated within a self-enclosed member for increased durability and rotational use.

Figure 1:
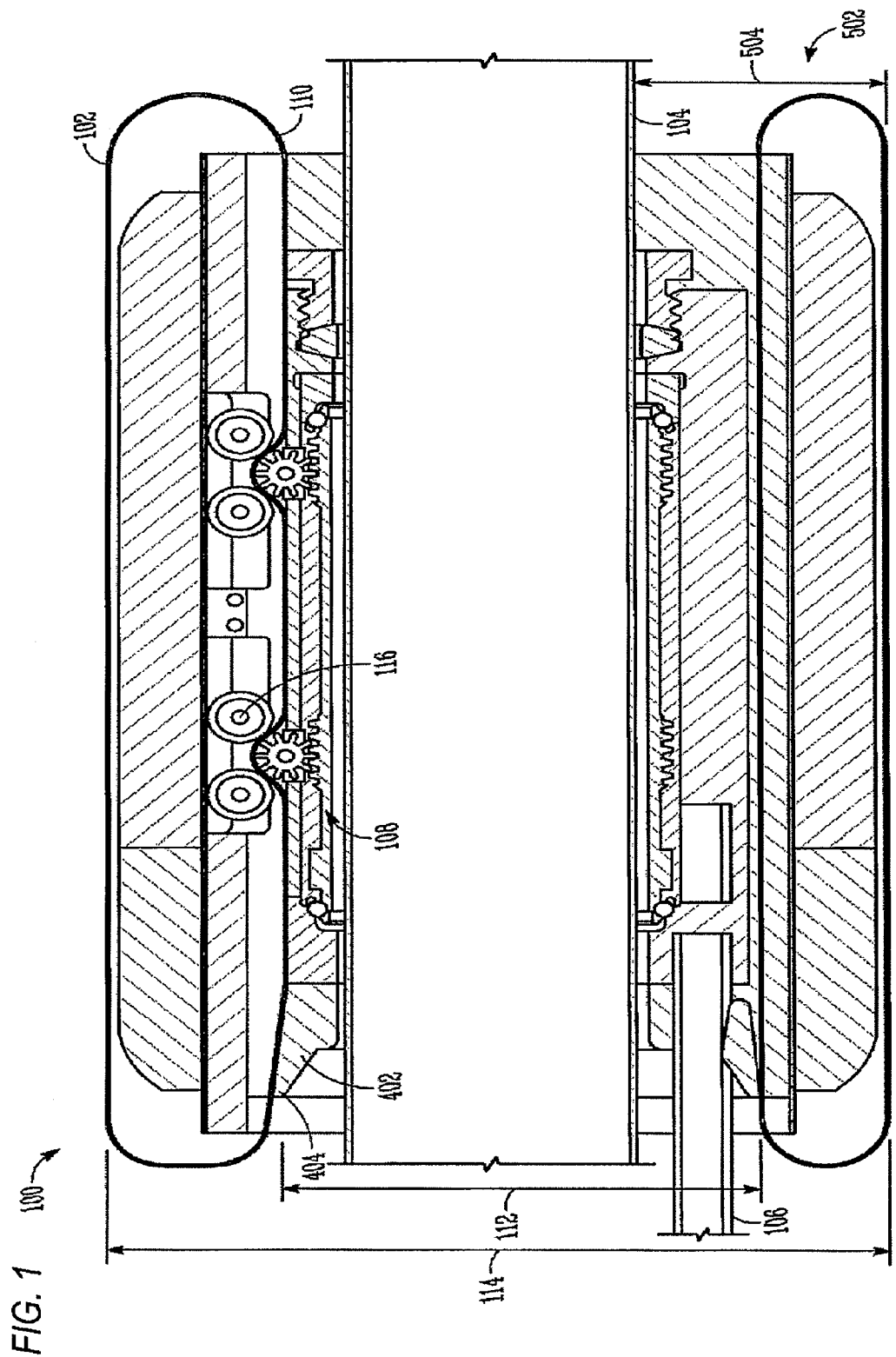
FIG. 1 illustrates an example of a cross-sectional view of a propellable apparatus and a payload, as constructed in accordance with at least one assembly embodiment.

As shown in FIG. 1, a propellable apparatus 100 can comprise a self-enclosed member 102 (e.g., self-enclosed tube, such as a toroidial membrane, or self-enclosed strips), which is sized and shaped to fit within and engage a cavity or lumen wall and be attachable to a payload 104 (e.g., an endoscope or other instrument). Rotation of the self-enclosed member 102 can create a propulsive force against the cavity or lumen wall. In various examples, power to actuate the self-enclosed member can be generated outside the cavity or lumen and be transmitted to the self-enclosed member 102 via one or more elongate drive members 106. At or near the self-enclosed member 102, the elongate members 106 can engage with one or more internal drive mechanisms 108 (e.g., one or more worm gears or motive drive wheels), which in turn can be engaged with an outer surface 110 of the self-enclosed member 102 as it passes through its smaller internal diameter 112. This allows the self-enclosed member 102 to engage the cavity or lumen wall as it travels through its larger diameter 114. In various examples, one or more rollers or skids 116 can be used to bias portions of the self-enclosed member 102 against an alternating sequence of peaks separated by respective grooves of one or more gears or wheels of the internal drive mechanisms 108.

Figure 2:
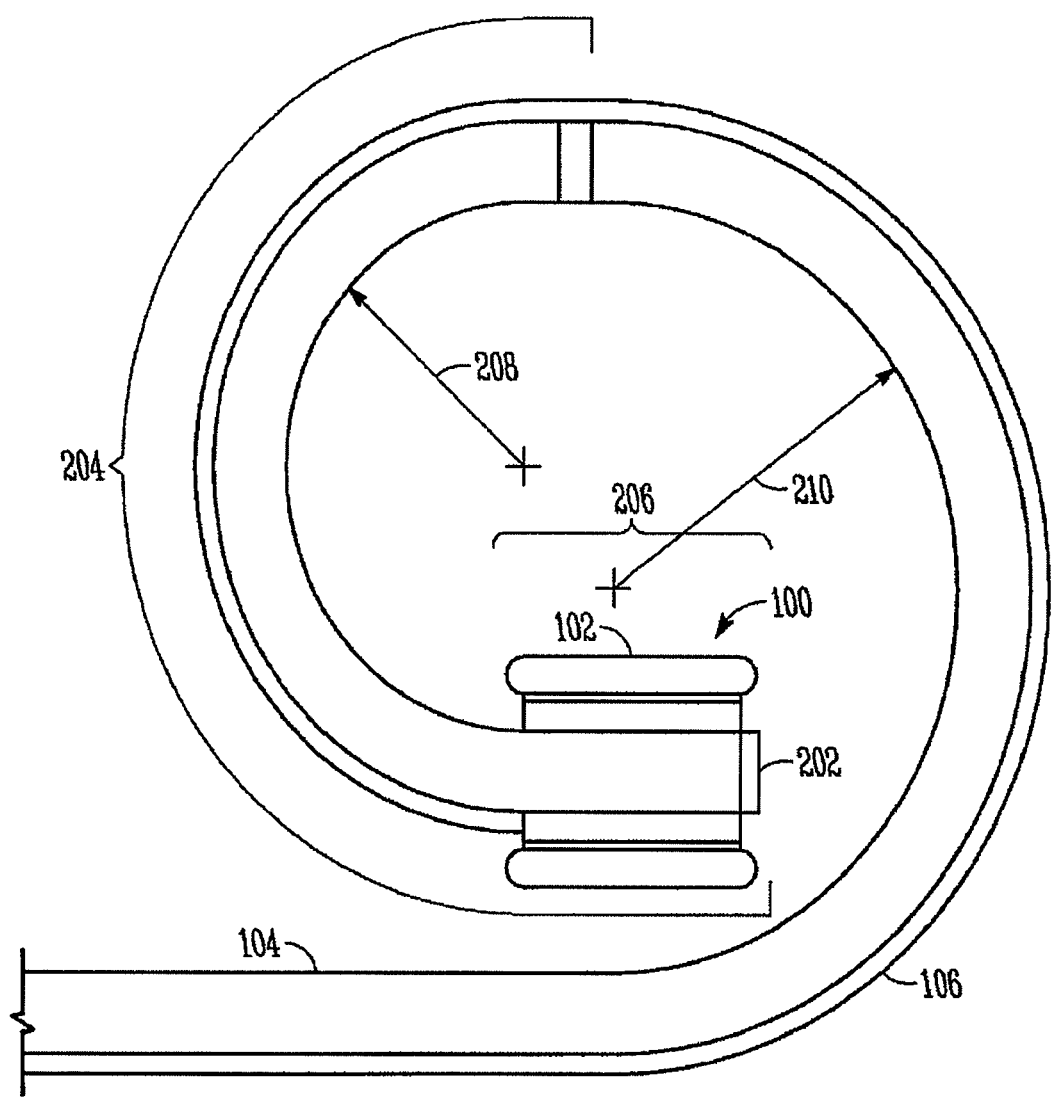
FIG. 2 illustrates an example of an attachment position between a propellable apparatus and a payload, as constructed in accordance with at least one assembly embodiment.

In some examples, as shown in FIG. 2, it has been found advantageous to attach a propellable apparatus 100 at a front-end tip portion 202 of a payload 104. Mounting the propellable apparatus 100 at the front-end tip portion 202 of the payload 104 can have advantages in some body anatomies for gathering lumen tissue, for example, over the tip of an endoscope and helping the endoscope tip navigate through sharp folds or narrowing diameters in a body cavity or lumen.

This mounting location can be advantageous in tortuous cavities or lumens, as compared to mounting the propellable apparatus 100 further back on the payload 104 behind an articulating section 204. The reasoning behind this is that the tissue of the cavity or lumen wall will have some drag against the tip of the payload 104, and this drag typically increases as the tip is flexed more for tortuous anatomy. If this drag over the tip is greater than the force with which the self-enclosed member 102 is acting to draw tissue over the propellable apparatus 100, then the apparatus 100 may fail to gather tissue over the tip of the payload 104. Conversely, if the propellable apparatus 100 is mounted at the front-end tip portion 202 of the payload 104, there can be little to no drag in front of the apparatus 102 resisting the rotating, self-enclosed member's 102 effect on the gathering of wall tissue over the tip of the payload 104.

Figure 3:
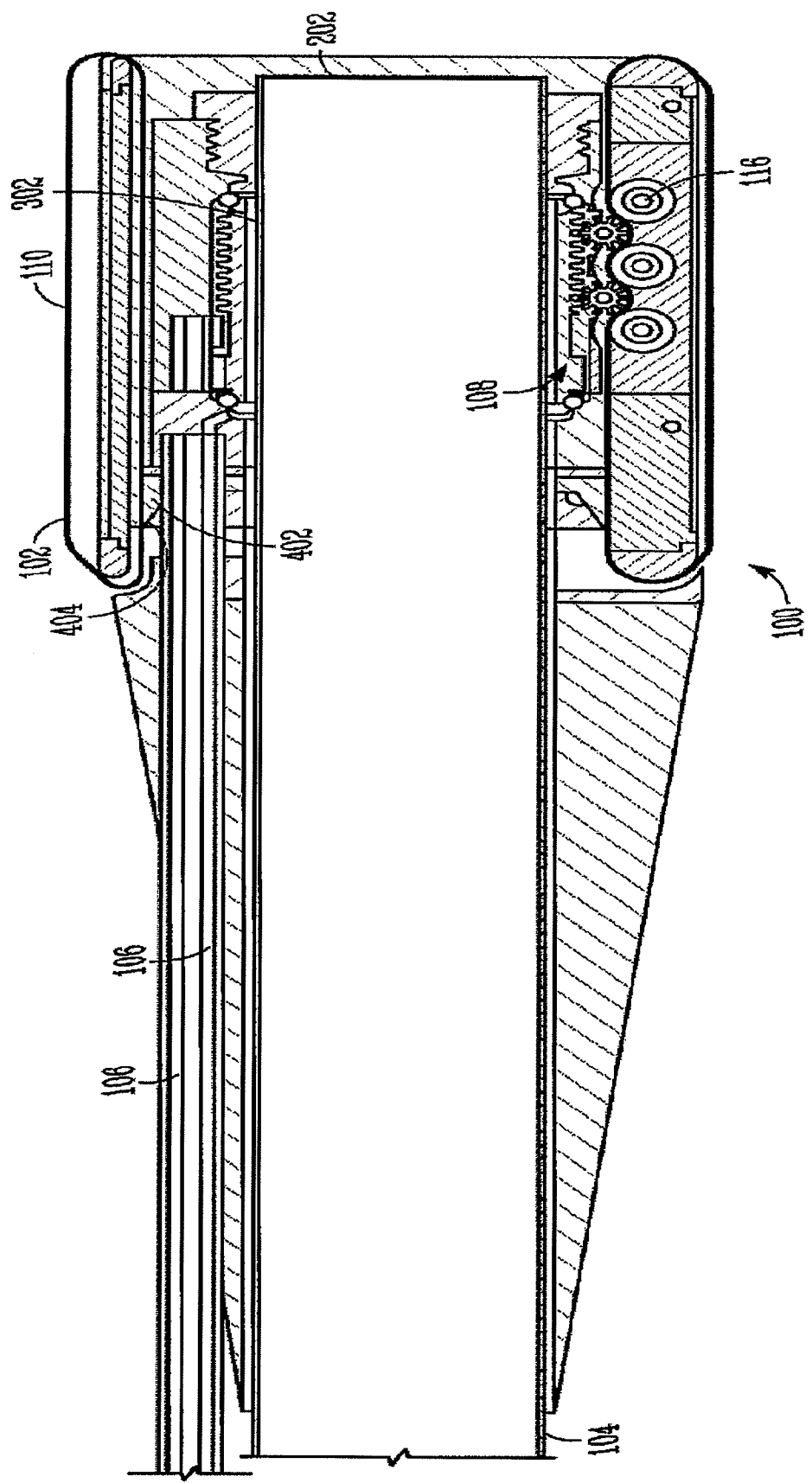
FIG. 3 illustrates an example of a cross-sectional view of a propellable apparatus, including a tapered-member, and a payload, as constructed in accordance with at least one assembly embodiment.

Mounting the propellable apparatus 100 at the front-end tip portion 202 of the payload 104 can, however, put demands on the propellable apparatus 100, which are not present if the apparatus 100 is mounted behind the payload's articulating, steerable section 204. The ends of endoscopes, for example, have flexible steerable sections that a physician can deflect using controls on a handle of the endoscope. One challenge of mounting the propellable apparatus 100 on the front-end tip portion 202 of the payload 104 is to not inhibit the physician's ability to control the articulation of the payload tip. The articulating section 204 of a scope is typically about 3 inches long and is located immediately adjacent an about 1 inch rigid section 206 at the tip which houses the scope's optics. To not inhibit the articulation an appreciable degree, the propellable apparatus 100 can be mounted on the rigid section 206 at the front-end tip portion 202 and the propellable apparatus 100 length can be about 1 inch in length, in some examples, for scopes having these typical dimensions. In other examples, the propellable apparatus 100 length can be less than about 1.5 inches, less than about 1.4 inches, less than about 1.3 inches, less than about 1.2 inches, less than about 1.1 inches, or less than about 1.0 inches, such that the apparatus length is less than a length of a rigid section 206 located at or near a front-end tip 202 of a payload 104. These lower limits can be advantageous for small bowel and other applications where relatively smaller and more articulatable payloads may be used. An example of a propellable apparatus 100 meeting this desired length is shown in the cross-sectional side view of FIG. 3. As compared to FIG. 1, it can be seen that the internal drive mechanisms 108 and opposing one or more rollers or skids 116 have been compressed in their spacing to yield a shorter overall apparatus 100 length.

A second aspect of mounting the propellable apparatus 100 at the front-end tip portion 202 of the payload 104 is that the articulating section 204 of the payload 104 is able to flex to a smaller radius of curvature 208 than the radius of curvature 210 of the body of the payload 104 behind the articulating region 204 (see, FIG. 2). In some typical colonoscopes, the radius of curvature at maximum flexing is about 1 inch for the articulating section and about 2 inches for the body of the scope. This can have implications for the apparatus elongate drive members 106 if the propellable apparatus 100 is mounted at the front-end tip portion 202 of the payload 104, as these drive members 106 may need to tolerate a smaller radius of curvature in use when the apparatus 100 is mounted at the front-end tip portion 202 of the payload 104 relative to being mounted behind the articulating section 204.

Rotating drive members 106 are subjected to oscillating stresses when they are flexed during rotation. These oscillating stresses can result in fatigue failure of the drive members 106, if the stresses are high enough. These stresses increase as the radius of curvature decreases for a given drive member 106 design. For this reason, it may be desirable to use drive members 106 that operate at lower oscillating stresses for a given radius of curvature when the propellable apparatus 100 is to be mounted at the front-end tip portion 202 of the payload 104.

One possible way of reducing the stresses due to bending is to use one or more smaller diameter drive members 106. The smaller diameter can decrease the stresses due to bending, however, the smaller diameter can also decrease the amount of torsional load the wire can carry. A second possible way to decrease the stresses in the drive members 106 due to bending can be to use a cable including wound filaments for each of the drive members 106 instead of a solid wire. Drive cables may be produced, for example, by winding small diameter filaments in a helical pattern around a central wire in a first direction, and further winding more small diameter filaments around the outside of the first helically wound filaments in a second, opposite direction. Additional small diameter filaments can further be wound over the opposite direction filaments, as needed or as desired. Having the helical filaments wound in more than one direction allows the resulting cable to transmit torque in both rotational directions without unacceptable unwinding of the wound filaments. Due to the smaller diameter of the individual filaments used, the drive members 106 can tolerate a smaller radius of curvature as compared to solid drive wires. This can allow use of a larger diameter cable than a solid drive wire for a given application. This can further provide greater flexibility in meeting both torsional and fatigue requirements for the one or more drive members 106.

When mounting a propellable apparatus 100 at the front-end tip portion 202 of a payload 104, a cable including small diameter filaments can be use for the entire length of the one or more drive members 106. A cable including small diameter filaments can also be used in a composite drive member 106 construction with the cable including filaments used for the length along the articulating section 204 of the payload 104 and a solid drive wire behind the articulating section 204 where the bending radius requirements are decreased. A composite drive member construction can be desirable to minimize propellable apparatus manufacturing costs, as the cable construction is likely to be more expensive than the solid drive wire. One example of a solid wire drive wire for a propellable apparatus 100 application is a straightened 400 kpsi stainless steel 0.022 inch diameter wire. One example of a cable including filaments that can be used for a propellable apparatus 100 application is a 0.050 inch cable produced by SS White(R) Technologies, Inc. of Piscataway, N.J., which includes four wires wrapped around a central wire and two sets of six wires wound around the four wires in an opposite direction. All of these individual filaments, in this example, are 0.007 inches in diameter.

A third challenge of mounting the propellable apparatus 100 at the front-end tip portion 202 of the payload 104 is that heat can build up at the tip. Endoscopes, for example, can include small lights at their tips projecting forward to allow the physician to see down a cavity or lumen with the optics mounted at the tip. These lights generate heat and this heat should be dissipated. If the heat were to build up and the temperature of the tip became excessively high, it can possibly degrade the image quality of the optics. It could also become a risk of damaging cavity or lumen wall bodily tissue that contacts the heated end of the scope.

Mounting the propellable apparatus 100 over the front-end tip portion 202 of the payload 104 could help insulate the tip, limiting the heat dissipation to adjacent bodily tissue. Additionally, the one or more gear power couplings 108 and drive members 206 interface could generate additional heat of its own. Thus, in some embodiments, it may be desirable to control the heat generated by the internal drive mechanisms 108 of the propellable apparatus 100. This can be done by, for example, minimizing the drive power input to the propellable apparatus 100 needed by minimizing the drag of the self-enclosed member 102 as it rotates. To this end, lubricious materials and coatings for the contact surfaces and the self-enclosed member 102 itself can be added. Heat reduction can also be addressed using a small amount of cooling water introduced inside the propellable apparatus 100. In one example, the cooling water can be introduced through a tubular member in the one or more drive members 106 (see, FIG. 3), which exits inside the propellable apparatus 100 in the internally-positioned drive mechanism 108 or in a lumen 302 between the propellable apparatus 100 and the payload surface.

In various examples, such as are shown in FIGS. 1, 3, 4, 5 and 7, the propellable apparatus 100 can include a wiper member 402. The present inventors have found that, in practice, it should be assured that bodily tissue or other cavity or lumen debris is not pulled via the self-enclosed member 102 into the internally-positioned drive mechanisms 108 as the self-enclosed member 102 rotates into its small diameter path 112 (see, FIG. 1). In FIG. 1, a wiper member 402 is shown mounted to a portion of the internal drive mechanism 108, with an edge 404.

Figure 4:
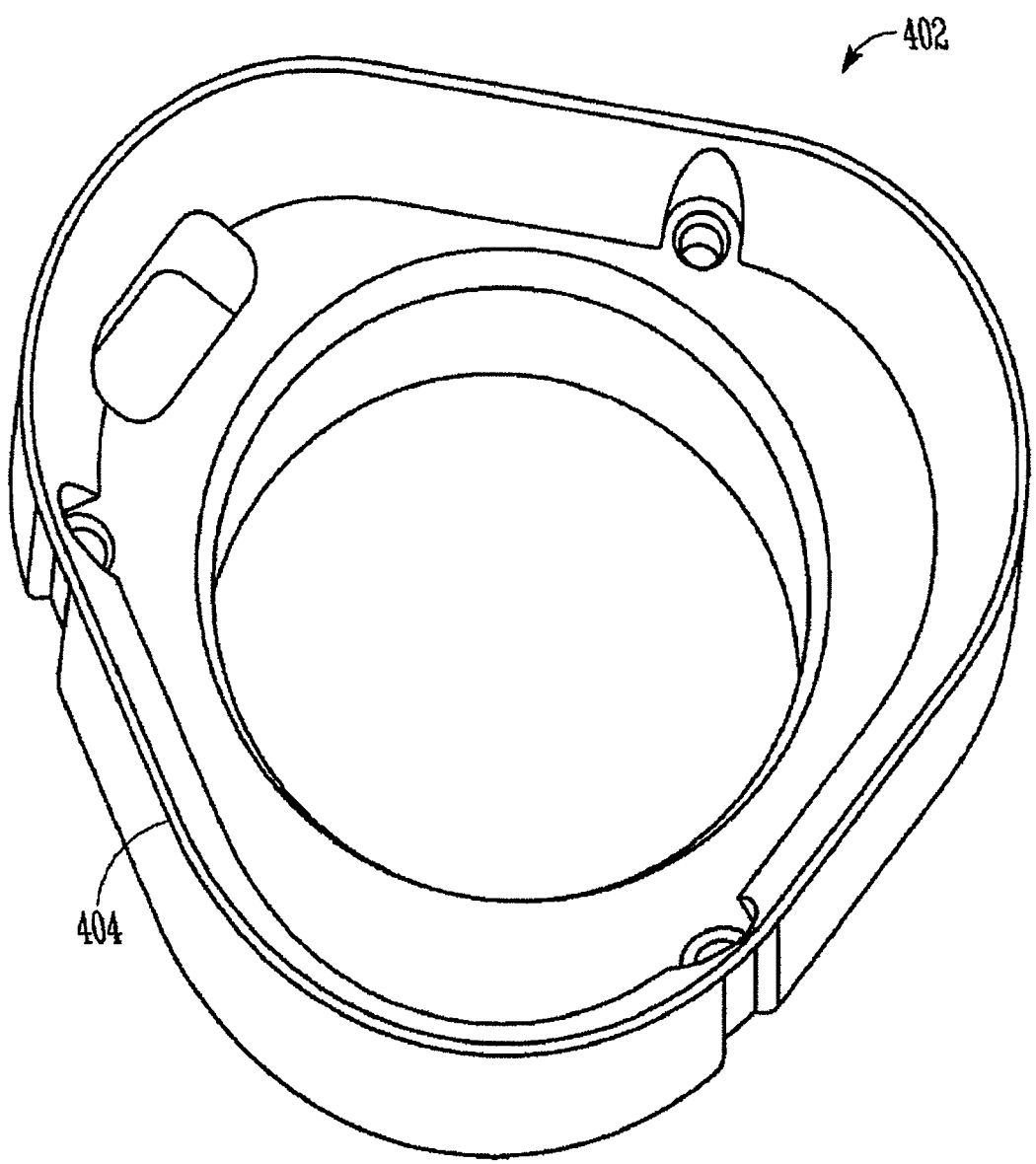
FIG. 4 illustrates an example of an isometric view of a wiper member positionable at an end of a propellable apparatus, as constructed in accordance with at least one embodiment.

The edge 404 presses against the self-enclosed member 102 as it passes into its smaller diameter 112 path. In various examples, the wiper member 402 is a component that can be added to the propellable apparatus 100 assembly to prevent or inhibit tissue or other cavity or lumen debris from being pulled into the internal mechanisms of the apparatus 100 by the rotating, self-enclosed member 102. The wiper member 402 can act like a squeegee to separate any tissue or other debris from sticking to an outer surface of the self-enclosed member 102. One example of an isometric view of a wiper member 402 is shown in FIG. 4.

Figure 5:
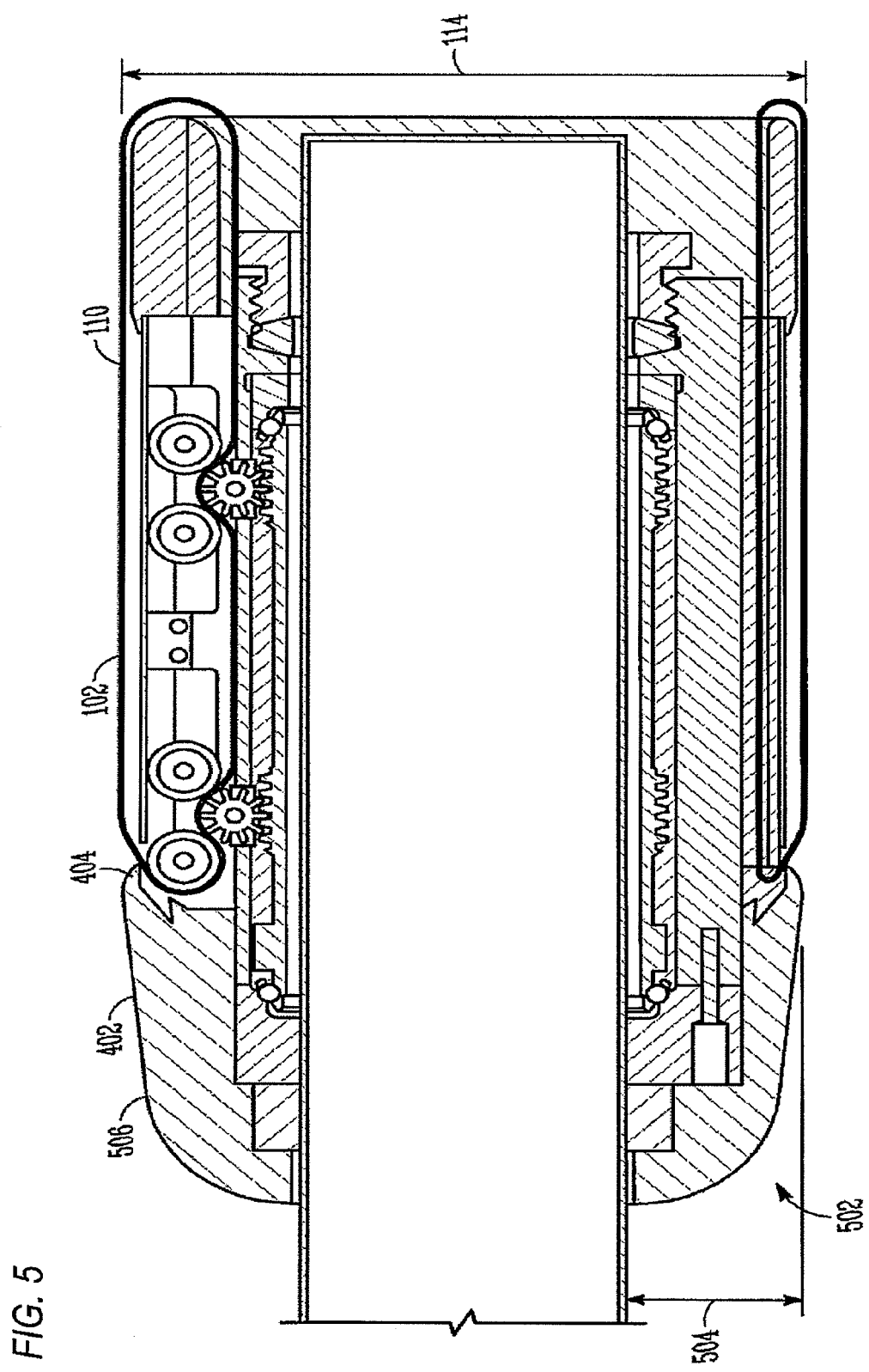
FIG. 5 illustrates an example of a cross-sectional view of a propellable apparatus, including a back-end positioned wiper and tapered member, and a payload, as constructed in accordance with at least one assembly embodiment.

As shown in FIG. 5, the wiper member 402 can also be placed against the outer surface 110 of the self-enclosed member 102 at or near its larger outer diameter 114. In various examples, the wiper member 402 can be rigid and shaped to substantially match the contour of the outer surface of the self-enclosed member 102, or it can be flexible and conform to this outer surface. The wiper member 402 can be made of a wide range of engineering polymers or metals. In one example, the wiper member 402 is made from Santoprene(R) 281 having a 55 MED durometer. In some examples, the wiper member 402 is made of a relatively lubricious polymer (e.g., fluoropolymers) to minimize the drag it adds to the rotation of the self-enclosed member 102. In some examples, the wiper member 402 is coated with a lubricious material, such as silicone oil or a hydrophilic coating.

In various examples of the propellable apparatus 100, such as the apparatus shown in FIG. 1, the back-end 502 includes a fairly abrupt diameter change 504 between the outer diameter 114 of the self-enclosed member 102 and a diameter of the payload 104 located behind it. In some examples, it can be desirable to have this diameter change 504 taper more gradually, such that there are few to no ledges to catch bodily tissue or other debris on as the propellable apparatus 100 is being withdrawn through a cavity or lumen. It may also be desirable to have the rigid length of the propellable apparatus 100 as short as possible to ease advancement through tortuous anatomy and to not inhibit payload 104 articulation when the propellable apparatus 100 is mounted on the front-end tip portion 202 of an articulating payload, such as an endoscope.

Figure 6:
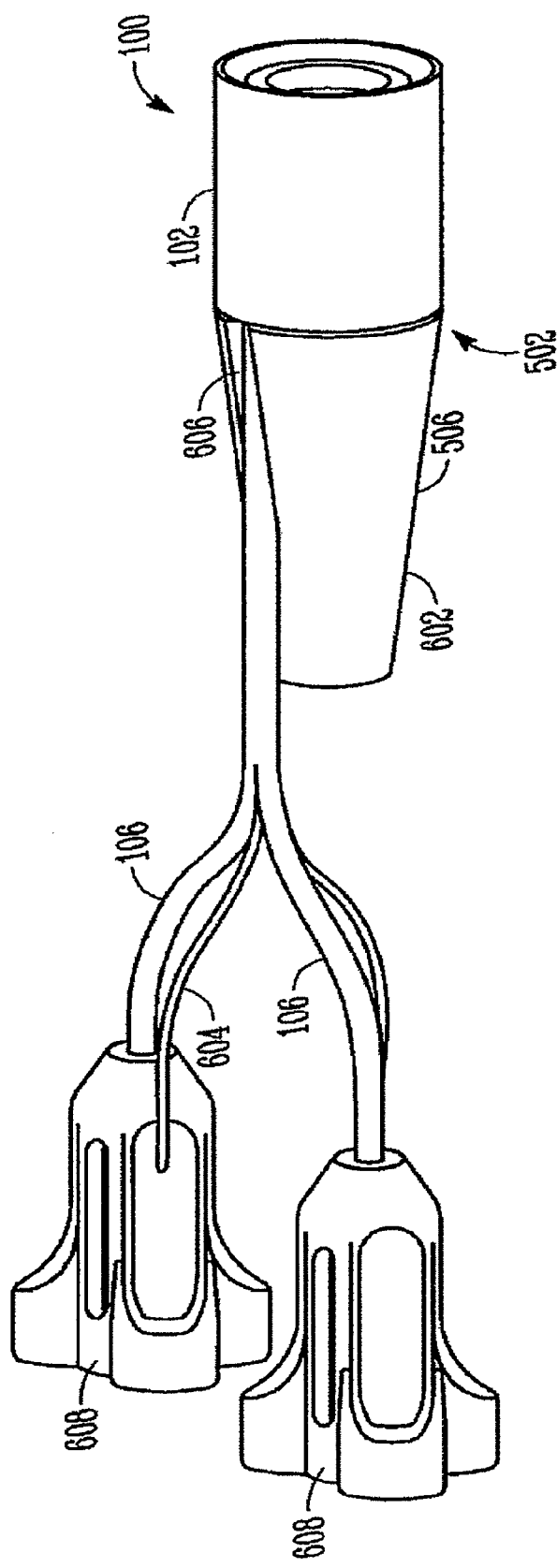
FIG. 6 illustrates an example of an isometric view of a propellable apparatus, including an actively expandable and contractible tapered member positioned at an apparatus back-end, associated drive members, and inflation/deflation tubes, as constructed in accordance with at least one embodiment.

It may be further desirable to have a tapered member (e.g., a wedge-shaped member) 506 that does not hinder the effectiveness of any propellable apparatus 100 components, such as the various wiper members discussed above. In one example, as shown in FIG. 6, the tapered member 506 is in the form a conically-shaped, actively inflatable balloon 602, which is sleeved over a portion of a payload 104 behind the propellable apparatus 100. In this way, the balloon 602, when inflated, creates a smooth tapered diameter transition from the back-end 502 of the rotating membrane to the surface of the payload 104. This inflatable balloon 602 can be attached to the back-end 502 of the propellable apparatus 100 such that its position relative to the back-end 502 is fixed. In some examples, one or more tubular members 604 to inflate or deflate the balloon can be included in the casing of the one or more drive members 106 of the propellable apparatus 100. In practice, this balloon 602 can be un-inflated and collapsed or otherwise contracted when the scope is being advanced forward in a cavity or lumen, assisted by the propellable apparatus 100 and its rotating, self-enclosed member. After reaching a target point in the cavity or lumen, such as the cecum during colonoscopy, the rotation of the self-enclosed member 102 can be stopped and the balloon can be 602 inflated. The payload 104 can then be withdrawn through the cavity or lumen as the operator (e.g., physician) does his/her inspection. It is believed that the presence of an activatable (e.g., actuatable) tapered member 506, such as the balloon 602, can minimize drag in the cavity or lumen when in a deflated state during advancement, and minimize risk of tissue or other debris hang up during withdrawal when in an expanded state.

Other options for the tapered member 506, and particularly the balloon 602, can be as follows. The balloon 602 can be made to be flexible so that it does not inhibit any desired flexing of the payload 104 beneath it. This could be valuable when the propellable apparatus 100 is mounted at the front-end tip portion 202 of the payload 104 and the balloon 602, at least in part, is mounted over the payload's articulating section 204 (see, FIG. 2). In one example, the balloon 602 is formed from sheet urethane having a durometer of about 80 A and a thickness of about 0.003 inches. The sheet urethane can be cut and heat sealed into a conical balloon shape having a diameter at one end approximately equal to the diameter of the rotating, self-enclosed member 102 of the propellable apparatus 100. The balloon 602 can be sealed down at its base to a cylindrical urethane tube having a diameter slightly larger than the diameter of the payload 104 it is sliding or otherwise advancing over. A groove 606 can be formed in the conical or otherwise shaped balloon 602, such as by heat sealing the balloon down to the urethane tube in one line along the length of the balloon 602. This groove 606 can act as a path for the one or more drive members 106 powering the rotating propellable apparatus 100 or the one or more tubular members 604 used to inflate or deflate the balloon 602. In some examples, the actual inflation and deflation of the balloon 602 can be done with a syringe and a stop cock on the end of the inflation tubular members 604 off the drive members 106, at or near their connection 608 to a motor controller.

Figure 7:
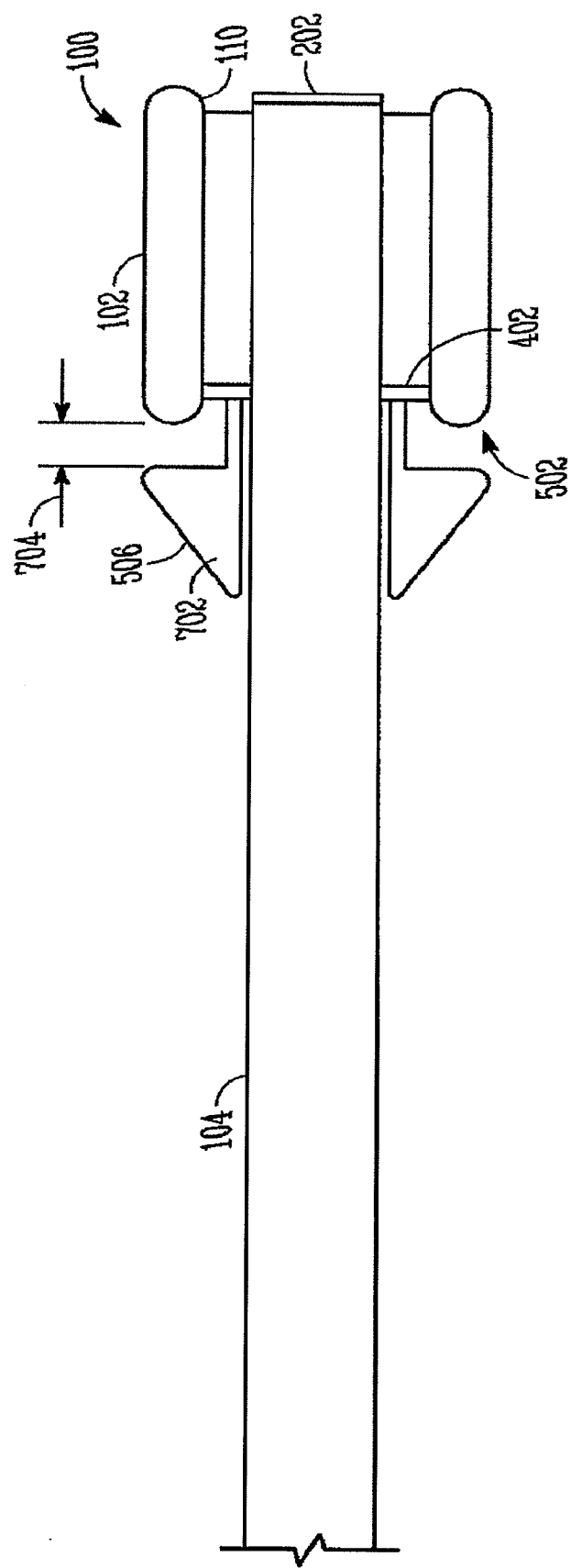
FIG. 7 illustrates an example of a schematic view of a propellable apparatus, including a back-end positioned tapered member mounted via a wiper member, and a payload, as constructed in accordance with at least one assembly embodiment.

In another example, as shown in FIG. 7, the tapered member 506 is achieved with a flexible polymer component 702 fixedly mounted to the propellable apparatus 100, such as via a wiper member 402. In this example, the tapered member 506 is passive and does not require actuation on the part of the operator (e.g., physician). The tapered member 506 of FIG. 5 shows a second variation of this approach. In some examples, as shown in FIG. 7, the tapered member 506 including a flexible polymer component 702 is connected behind the wiper member 402 and leaves clearance 704 off of the rotating, self-enclosed member 102 to minimize the risk of creating a tissue or other debris pinch point. In FIG. 5, the wiper member 402 is integrated into the tapered back piece 506 and has the wiper edge 404 on the outer surface of the rotating, self-enclosed member 102.

Figure 8:
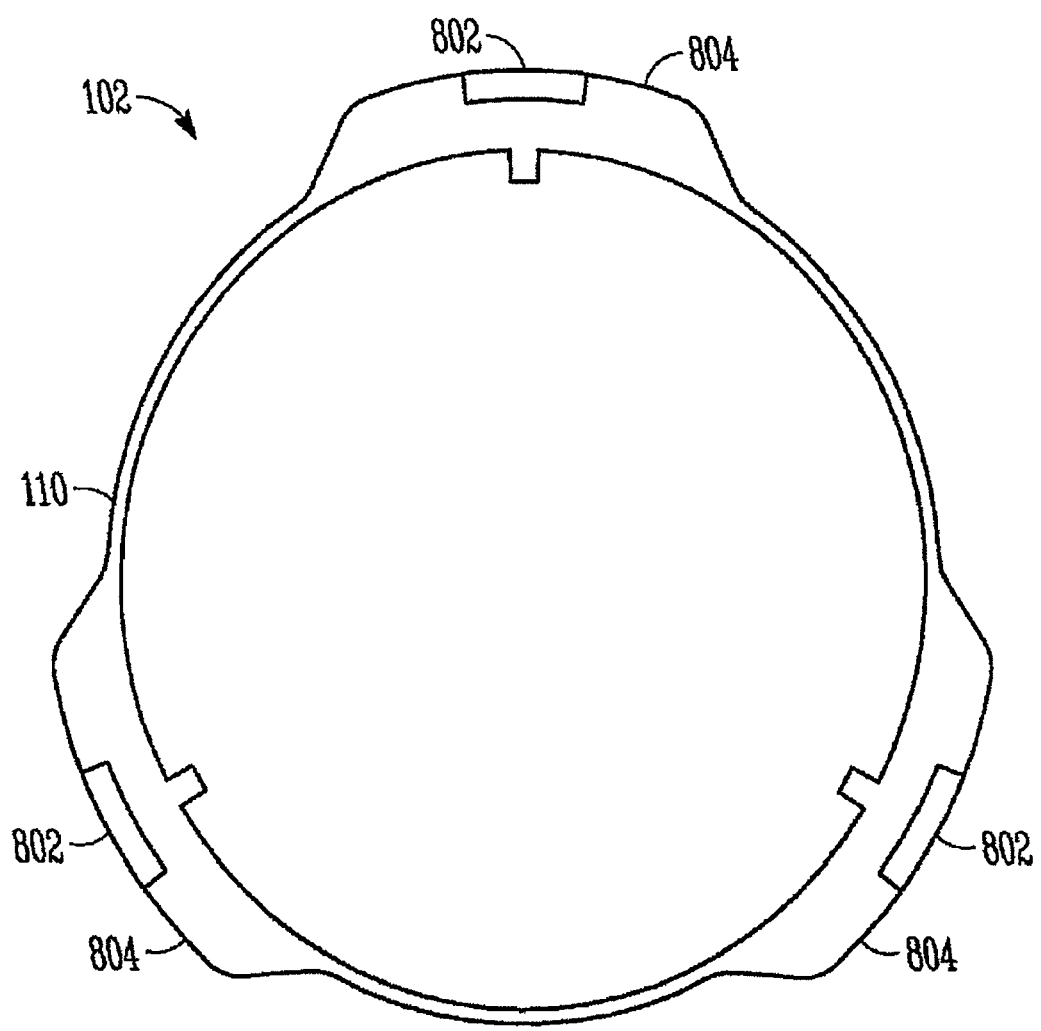
FIG. 8 illustrates an example of a cross-sectional view of a self-enclosed member, as constructed in accordance with at least one embodiment.
Figure 9:
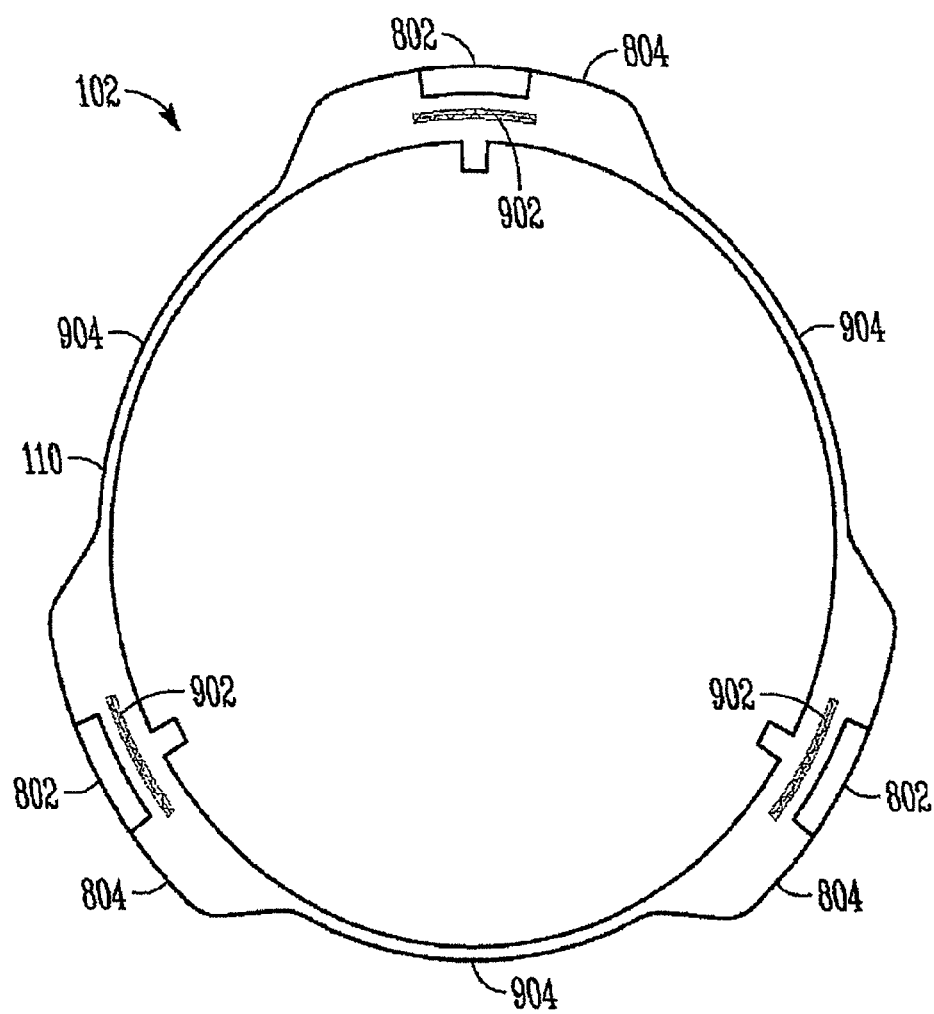
FIG. 9 illustrates an example of a cross-sectional view of a self-enclosed member including a reinforcing member, as constructed in accordance with at least one embodiment.
Figure 10:
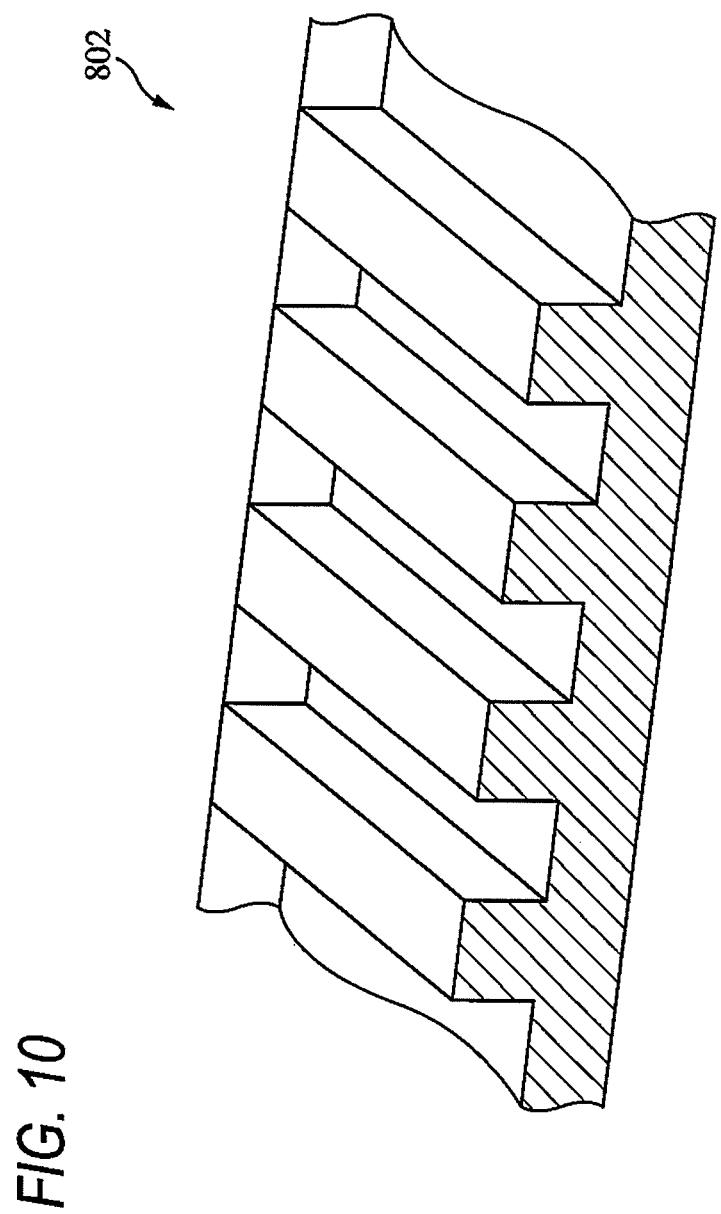
FIG. 10 illustrates an example of a cross-sectional view of a tread including an alternating sequence of peaks which have square shapes and which are separated by respective grooves, as constructed in accordance with at least one embodiment.
Figure 11:
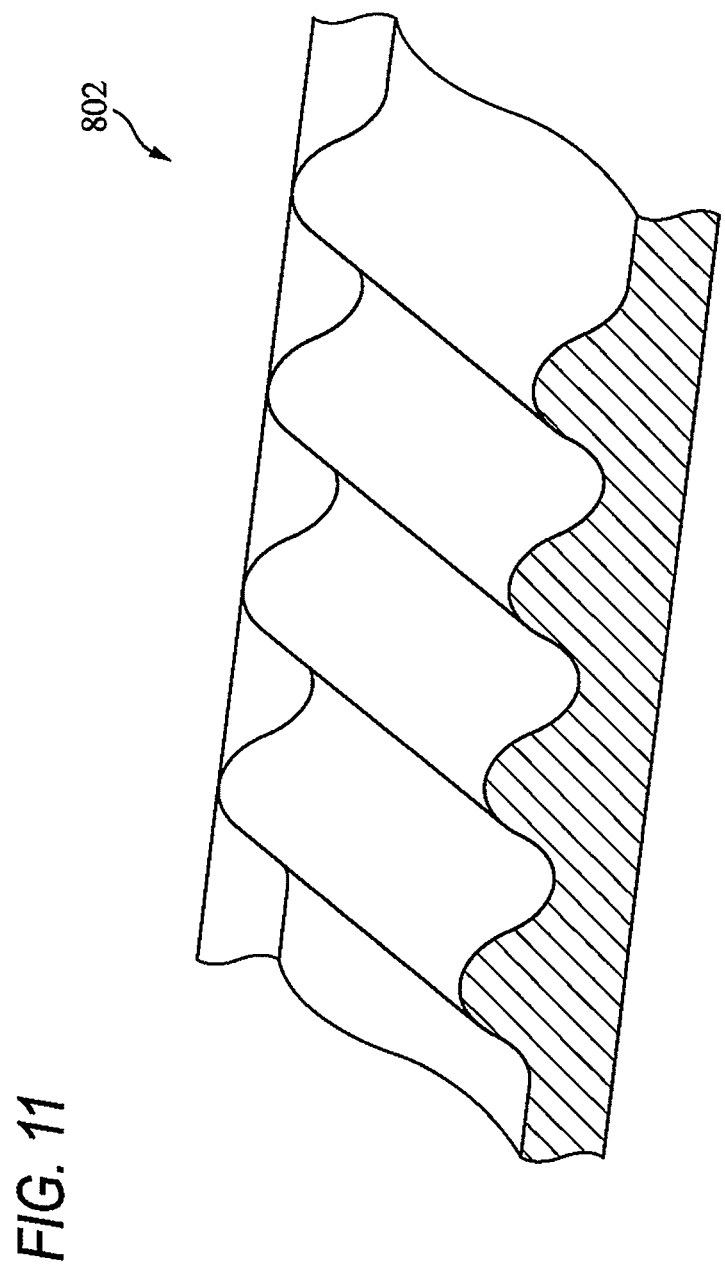
FIG. 11 illustrates an example of a cross-sectional view of a tread including an alternating sequence of peaks which have rounded shapes and which are separated by respective grooves, as constructed in accordance with at least one embodiment.

In various examples, as shown in FIGS. 8 and 9, the propellable apparatus 100 includes a self-enclosed member 102 having one or more of a thicker walled section 804, a tread 802, a reinforcing member 902 or a bead. The thicker walled section 804 (which is a second section) is thicker or stiffer than other section in the self-enclosed member 102 (which is a first section). The thicker walled section 804 (the second section) may have a portion which thickness varies gradually adjacent the other section (the first section) in the self-enclosed member 102. Additionally, the thicker walled section 804 (the second section) may have a portion which elasticity or which stiffness varies gradually adjacent the other section (the first section) in the self-enclosed member 102. In various examples, the self-enclosed member 102 can be configured to decrease transmission loss thereto of the driving forces provided by the internal drive mechanisms 108. In some examples, at least a portion of the outer surface of the self-enclosed member 102 can include a tread 802 having an alternating sequence of peaks separated by respective grooves (e.g., teeth), which are configured to engage with the alternating peaks and grooves of one or more gears or wheels of the internal drive mechanisms 108 (see, FIG. 1). As shown in FIGS. 10 and 11, each peak may have a square shape or a rounded shape. Each peak is arranged obliquely with respect to a traveling direction (moving direction of the relative movement between the self-enclosed member and the cavity or lumen wall) of the self-enclosed member 102. As shown in FIG. 1, these gears or wheels may be engaged against the tread by biasing rollers or skids 116 positioned inside the self-enclosed member 102. Additionally, beads are under a portion where the internal drive mechanisms 108 engage with the thicker walled sections 804.

In use, the gears of the drive mechanisms 108 may skip or slip over the treads in the surface of the self-enclosed member 102 if enough rotational drag is placed on the member 102. This skipping or slipping can also occur if the self-enclosed member 102 has a smooth surface (e.g., without a tread). In addition, the skipping or slipping can get worse if the self-enclosed member 102 is relatively more elastic and can stretch as a result of increased rotational drag on the member 102. Minimizing the skipping or slipping of the self-enclosed member 102 over the gears can be desirable both for repeatable performance and because the skipping or slipping can accelerate the wear of the member 102 on the gears.

Engagement between the self-enclosed member 102 and the gears or wheels of the internal drive mechanisms 108 can be improved by having higher pressure between the rollers or skids 116 and the gears or wheels so that the member 102 is held tighter against the gears or wheels. Even if no skipping occurs, there can be a degree of wear on the self-enclosed member 102 by the gear or wheel contacting the teeth in normal use. As the wear on the self-enclosed member 102 advances, the member 102 outer surface can become cut and develop frayed edges on these cuts. This cutting and fraying can further decrease the engagement of the gears or wheels of the internal drive mechanism 108 and the self-enclosed member 102 until the member 102 slows and eventually stalls or the frayed ends become wrapped in the gear or wheel coupling and abruptly stalls the apparatus 100. Thus, FIG. 9 illustrates one way of reinforcing the self-enclosed member 102 to significantly increase its wear resistance and significantly decrease its elasticity, thereby improving its rotational and overall performance.

FIG. 8 illustrates a cross-sectional view of one example of a self-enclosed member 102 for use in a propellable apparatus 100. In this sectional example, the self-enclosed member 102 is shown as a cylinder in an intermediate state during manufacture, before it is rolled into a toroid and seamed to itself. The self-enclosed member 102 can be made of a polymer such as a urethane (e.g., Stevens Urethane 1880 having a durometer of about 80-85 A, and produced by Stevens Urethane of Easthampton, Mass.). Urethanes are generally tough polymers with good flexibility, and this combination makes them adequate candidates for the self-enclosed member 102 material.

FIG. 9 illustrates a cross-sectional view of another example of a self-enclosed member 102 having a reinforcing member 902 (e.g., reinforcing mesh) embedded in the member 102 wall. The reinforcing member 902 (which is a second layer) has less elasticity than other portion of the member 102 wall (which is a first or third layer). And, the reinforcing member 902 (the second layer) is sandwiched between materials (which are first and third layers) being more flexible than the reinforcing member 902. As shown, the self-enclosed member 102 of this example includes three thicker walled sections 804 around its circumference with treads 802 in the sections 804 to match up and align with the gears or wheels of the internal drive mechanism 108 at three locations, for example, around the circumference of the propellable apparatus 100. In this reinforcing example, a reinforcing member 902 is embedded in the sections 804 beneath the treads 802. And, the treads 802 are on the other portion of the member 102 wall except for the reinforcing member (the first layer). As such, the reinforcing member 902 is positioned under the gears or wheels, where it is effective both in enhancing durability and reducing the elasticity of the sections 804. These reinforcing members 902 can be made from a variety of polymer meshes. Some candidate materials include, but are not limited to, peek, nylon, or polyester. In one example, the thickness of these thicker walled sections 804 can be about 0.012 inches and the reinforcing members 902 can be made of a weave of about 0.002 inch fibers in a 200*200 mesh.

The reinforcing members 902 can be molded into the self-enclosed member wall by, for example, layering strips of urethane around the reinforcing material inside a mold and then pressing and heating the layers together to melt the urethane and flow it in or around the reinforcing material. In the example shown, the reinforcing members 902 are only used under the treads 802 so the stiffer reinforcing material is not present in the thinner walled web sections 904 outside the gear paths and consequently doesn't impact the stiffness of the self-enclosed member 102 in these areas. It could also be beneficial to have the reinforcing members 902 cover a bigger area of the section 804 width, extend into or replace the web sections 904, or be positioned in a different height in the thickness of the self-enclosed member 102.

Figure 12:
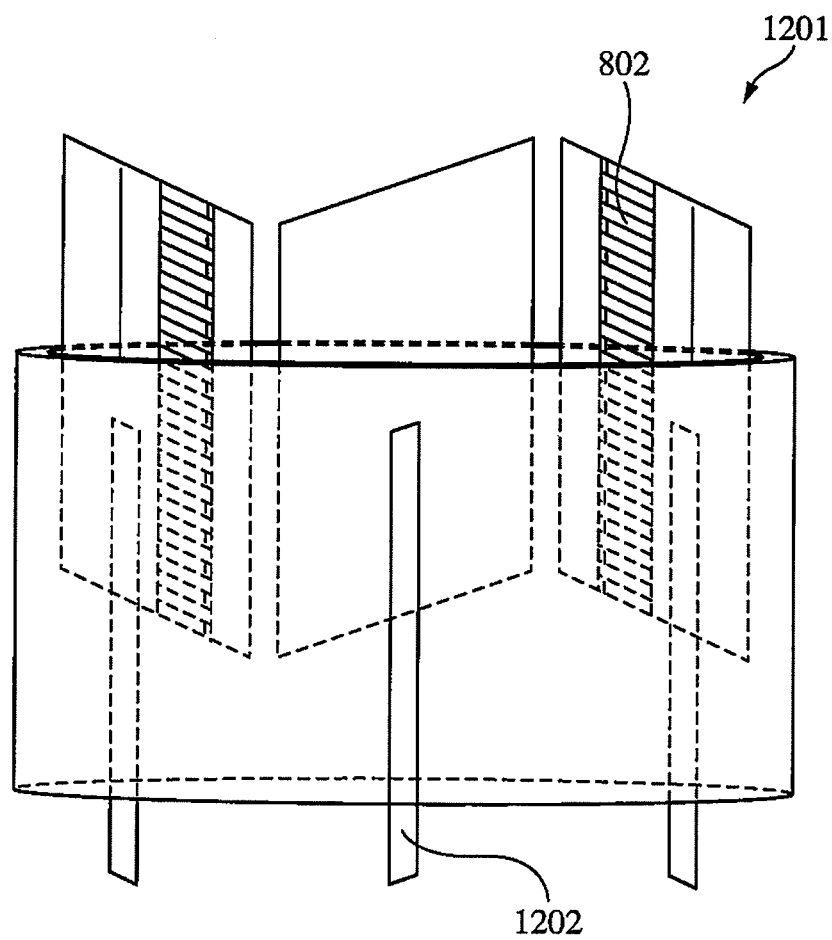
FIG. 12 illustrates an example of a schematic view of a tube including a first and second sections, beads, treads, as constructed in accordance with at least one embodiment.
Figure 14:
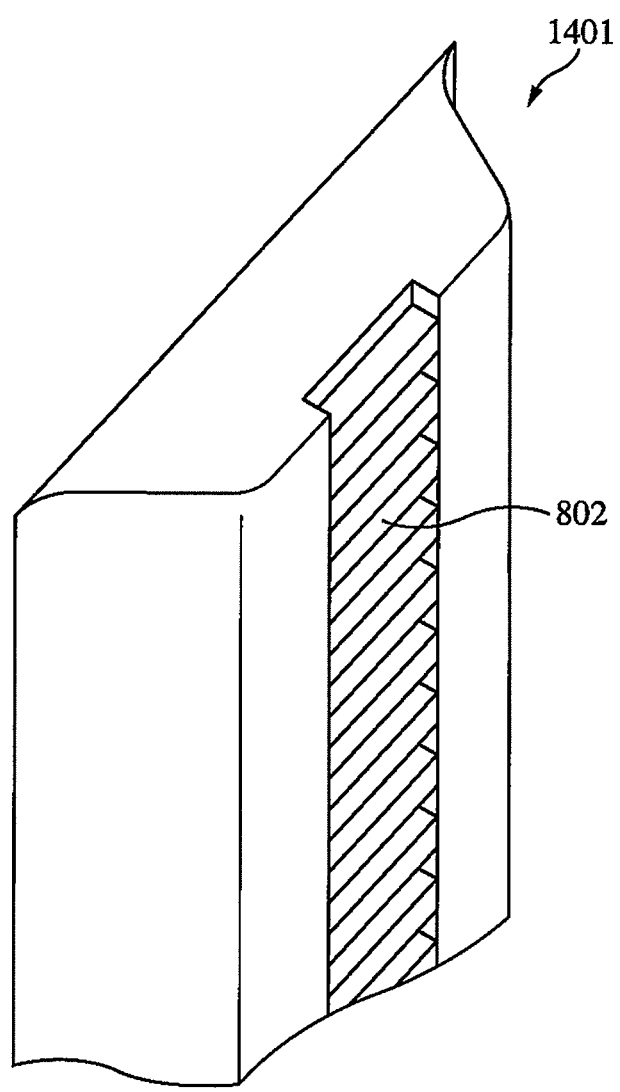
FIG. 14 illustrates an example of a magnified view of an edge of a second section in a tube including a tread and grooves, as constructed in accordance with at least one embodiment.

FIG. 12 illustrates a tube 1201 in an intermediate state during manufacture of the self-enclosed member 102. FIGS. 13A and 13B illustrate development views of the tube 1201. FIG. 13A illustrates one side of the development view of the tube 1201 including beads. FIG. 13B illustrates the other side of the development view of the tube 1201 including the first and second sections and treads. The tube 1201 has a body portion and two edges. The body portion of the tube 1201 is configured to be rolled into a toroid along with an axis direction of the tube 1201 by connecting both two edges of the tube 1201. Thickness of each edge of the tube 1201 is thinner than the body portion of the tube 1201. Because each edge of the tube is thinner than the body portion, the toroid has uniform thickness along the axis direction when each edged is connected each other. Each edge of the tube 1201 includes the first and second sections. The tube 1201 may have at least one tread 802 which is arranged along with the axis direction of the tube 1201. As shown in FIG. 14, each edge of the second section 1401 is parallel to the grooves of the tread 802. The tube 1201 may have at least one bead 1202 which is arranged along with the axis direction of the tube 1201. Each edge of the tube 1201 includes each edge of the bead 1202, which are connected each other. Each edge of the bead 1202 is oblique with respect to the axis direction of the tube 1201. One edge of the bead 1202 protrudes from the tube edge along the axis direction. The other edge of the bead 1202 ends just before the tube edge so as to accommodate the protruded bead edge when the both edges of the tube are connected each other.

Closing Notes:

The present inventors have recognized that (1) it can sometimes be advantageous to attach the propellable apparatus at a front-end tip portion of a payload, (2) a propellable apparatus having a relatively short length (e.g., between about 0.8 inches and about 1.5 inches) does not limit articulation of a flexible payload, having a separately controllable articulating capability, an appreciable degree when it is mounted at or near the front-end thereof, (3) drive members made of flexible cable including wrapped filaments allows for adequate flexing without reaching unacceptable internal stress levels during rotation, (4) one or more wiper members can be added to the propellable apparatus, such as at one or both apparatus ends, to prevent tissue from engaging with the apparatus drive mechanism, (5) a tapered member can be added to a back-end of the propellable apparatus to facilitate removal of the apparatus from a cavity or lumen, and (6) one or more reinforcing members can be integrated within a self-enclosed member for increased durability and rotational use.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the term "back-end" is used to refer to a portion of a propellable apparatus, which is configured to be located closer to a cavity or lumen orifice after insertion of the apparatus therein. In contrast, the term "front-end" is used in this document to refer to a portion of the propellable apparatus, which is configured to be located farther from the cavity or lumen orifice after insertion and which leads the apparatus through the cavity or lumen.

In the appended claims, the terms "including" and "in which" are used as the plain-English equivalents of the respective terms "comprising" and "wherein." Also, in the following claims, the terms "including" and "comprising" are open-ended, that is, a system, propellable apparatus, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. $1.72 (b), to allow the reader to quickly ascertain the nature of the technical disclosure. It is submitted with the understanding that it will not be used to interpret or limit the scope or meaning of the claims.

What is claimed is:
1. A propellable apparatus comprising:
 a self-enclosed member configured to fit within and partially engage a cavity or lumen wall, the self-enclosed member including at least one first section and at least one second section which is thicker or stiffer than at least one first section, the self-enclosed member defining a central cavity and having an interior volume;
an internal drive mechanism engageable with the second section, thereby providing relative movement between the self-enclosed member and the cavity or lumen wall,
wherein the second section includes first layer and second layer which has less elasticity than the first layer.

2. The propellable apparatus of claim 1, wherein
the second section includes a portion which thickness varies gradually adjacent the first section, or
the second section includes a portion which stiffness varies gradually adjacent the first section.

3. The propellable apparatus of claim 2, wherein
the second layer is embedded in the second section under a portion where the internal drive mechanism engages with the second section.

4. The propellable apparatus of claim 1, wherein
the second section includes third layer which has more elasticity than the second layer, and
the second layer is sandwiched between the first and third layers.

5. The propellable apparatus of claim 1, wherein
the internal drive mechanism includes at lease one gear which engages with the second section,
the second section includes at lease one tread which engages with the gear, and
the second layer is embedded in the second section under a portion of the tread.

6. The propellable apparatus of claim 5, wherein
each tread is on the first layer of the second section.

7. The propellable apparatus of claim 5, wherein
each tread includes an alternating sequence of peaks separated by respective grooves, and
each peak includes a square shape.

8. The propellable apparatus of claim 5, wherein
each tread includes an alternating sequence of peaks separated by respective grooves, and
each peak includes a rounded shape.

9. The propellable apparatus of claim 7, wherein
each peak is arranged obliquely with respect to a moving direction of the relative movement.

10. The propellable apparatus of claim 1, wherein
the self-enclosed member includes:
an inner surface which defines an enclosed region; and
an outer surface which turns outwardly to engage the cavity or lumen wall in addition to turning inwardly to a central region,
beads are on the inner surface of the self-enclosed member, and
each bead is under a portion where the internal drive mechanism engages with the second section.

11. A tube comprising:
a body portion and two edges, wherein
the body portion is configured to be rolled into a toroid along with an axis direction of the tube by connecting both edges of the tube each other, and
the toroid includes a self-enclosed member configured to fit a self-enclosed member configured to fit within and partially engage a cavity or lumen wall, the self-enclosed member including at least one first section and at least one second section which is thicker or stiffer than at least one first section, the self-enclosed member defining a central cavity and having an interior volume;
wherein the second section includes first layer and second layer which has less elasticity than the first layer.

12. The tube of claim 11, wherein
thickness of each edge of the tube is thinner than thickness of the body portion of the tube.

13. The tube of claim 11, wherein
each edge of the tube includes the first and second sections,
at least one tread that is arranged along with the axis direction of the tube, wherein
each tread includes an alternating sequence of peaks separated by respective grooves, and
each edge of the second section is parallel to the grooves.

14. The tube of claim 11, wherein
a bead is arranged along with the axis direction of the tube,
each edge of the tube which is connected each other includes each edge of the bead, and
each edge of the bead is oblique with respect to the axis direction of the tube.

15. The tube of claim 11, wherein
a bead is arranged along with the axis direction of the tube,
one edge of the bead protrudes from the tube edge along the axis direction, and
the other edge of the bead ends just before the tube edge so as to accommodate the protruded bead edge when the both edges of the tube are connected each other.

* * * * *